(12) United States Patent
Masotti et al.

(10) Patent No.: US 11,517,758 B2
(45) Date of Patent: Dec. 6, 2022

(54) DELIVERY DEVICE WITH COAXIAL CABLE, APPARATUS COMPRISING SAID DEVICE AND METHOD

(71) Applicants: EL.EN. S.P.A., Calenzano (IT); Daniele Ignesti, Florence (IT)

(72) Inventors: Leonardo Masotti, Sesto Fiorentino (IT); Mauro Galli, Sesto Fiorentino (IT); Riccardo Stocchi, Seano (IT); Paolo Corsini, Prato (IT); Marco Bini, Pistoia (IT); Amleto Ignesti, Vicchio (IT); Cristiano Riminesi, Florence (IT); Samuele Beni, Cavriglia (IT); Laura Pieri, Laterina PergineValdarn (IT); Alberto Calligaro, Solano del Lago (IT)

(73) Assignee: EL.EN. S.P.A., Florence (IT)

(*) Notice: Subject to any disclaimer, the term of this patent is extended or adjusted under 35 U.S.C. 154(b) by 494 days.

(21) Appl. No.: 16/299,671

(22) Filed: Mar. 12, 2019

(65) Prior Publication Data
US 2019/0255347 A1    Aug. 22, 2019

Related U.S. Application Data

(63) Continuation-in-part of application No. 16/081,631, filed as application No. PCT/IB2017/051215 on Mar. 2, 2017.

(30) Foreign Application Priority Data

Mar. 4, 2016   (IT) .......................... UA2016A001370

(51) Int. Cl.
*A61N 2/02*    (2006.01)
*A61N 1/40*    (2006.01)
(Continued)

(52) U.S. Cl.
CPC ............ *A61N 2/02* (2013.01); *A61B 18/1815* (2013.01); *A61N 1/403* (2013.01); *A61N 2/004* (2013.01);
(Continued)

(58) Field of Classification Search
CPC .......... A61N 2/02; A61N 1/403; A61N 2/004; A61B 18/1815; A61B 2018/183; A61B 2018/00023; A61B 2018/00464
(Continued)

(56) References Cited

U.S. PATENT DOCUMENTS 5,507,790 A * 4/1996 Weiss ....................... A61N 1/40
                                                              128/897
5,769,879 A * 6/1998 Richards ................ A61N 5/025
                                                              607/101

(Continued)

FOREIGN PATENT DOCUMENTS

WO      2009075904 A1    6/2009

*Primary Examiner* — Linda C Dvorak
*Assistant Examiner* — Annabeth E Rodriguez
(74) *Attorney, Agent, or Firm* — McGlew and Tuttle, P.C.

(57) ABSTRACT

The device includes an outer conductor and an inner conductor arranged approximately coaxial with each other. The outer conductor surrounds the inner conductor. The outer conductor and the inner conductor are arranged and configured to generate an electromagnetic field with lines of force extending from a front surface of the inner conductor to a front surface of the outer conductor. The device further includes an energy delivery window arranged in front of the outer conductor and the inner conductor.

10 Claims, 6 Drawing Sheets

(51) Int. Cl.
*A61N 2/00* (2006.01)
*A61B 18/18* (2006.01)
*A61B 18/00* (2006.01)

(52) U.S. Cl.
CPC ............... *A61B 2018/00023* (2013.01); *A61B 2018/00464* (2013.01); *A61B 2018/183* (2013.01)

(58) Field of Classification Search
USPC .......................................................... 606/33
See application file for complete search history.

(56) References Cited

U.S. PATENT DOCUMENTS

| | | |
|---|---|---|
| 2003/0130711 A1 | 7/2003 | Pearson et al. |
| 2004/0243200 A1 | 12/2004 | Turner et al. |
| 2007/0073367 A1* | 3/2007 | Jones ................... A61B 18/203 607/89 |
| 2009/0157068 A1 | 6/2009 | Kallel et al. |
| 2010/0137857 A1 | 6/2010 | Shroff et al. |
| 2010/0280509 A1 | 11/2010 | Muller et al. |
| 2011/0028898 A1* | 2/2011 | Clark, III ......... A61B 17/32002 604/93.01 |
| 2011/0077634 A1 | 3/2011 | Brannan |
| 2014/0350401 A1 | 11/2014 | Sinelnikov |
| 2015/0351838 A1* | 12/2015 | Deem ....................... A61N 5/02 606/33 |

\* cited by examiner

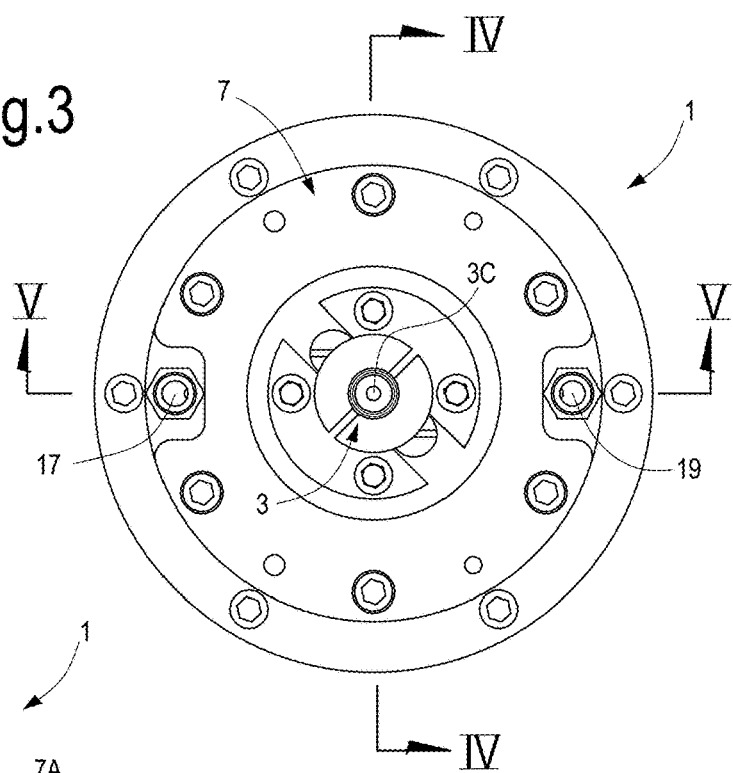
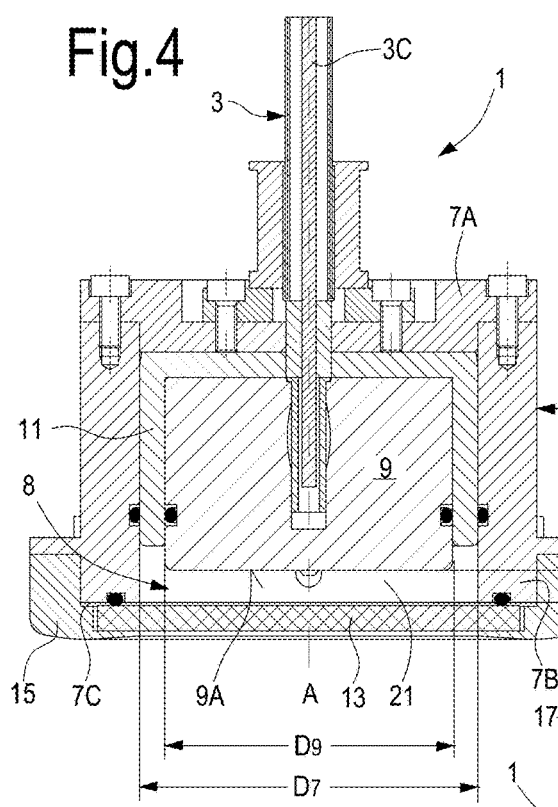
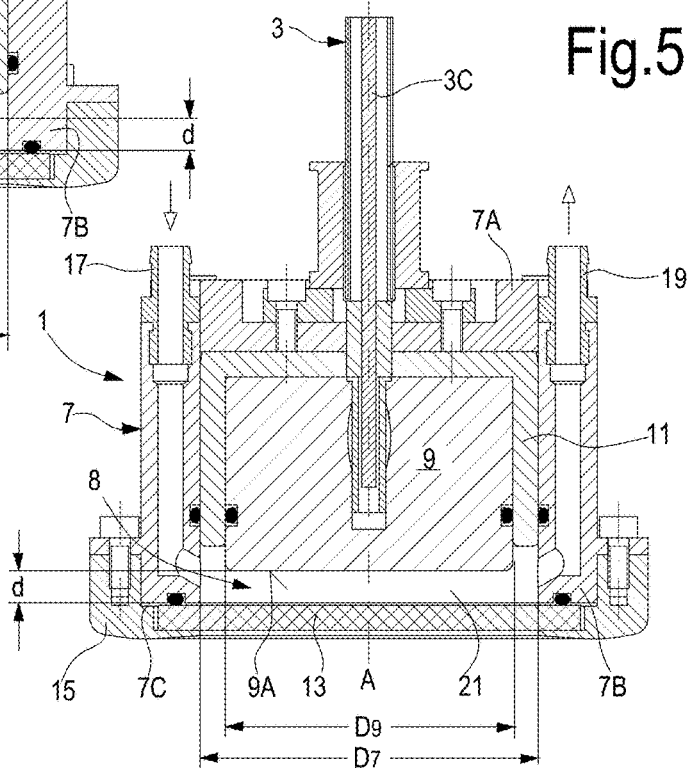

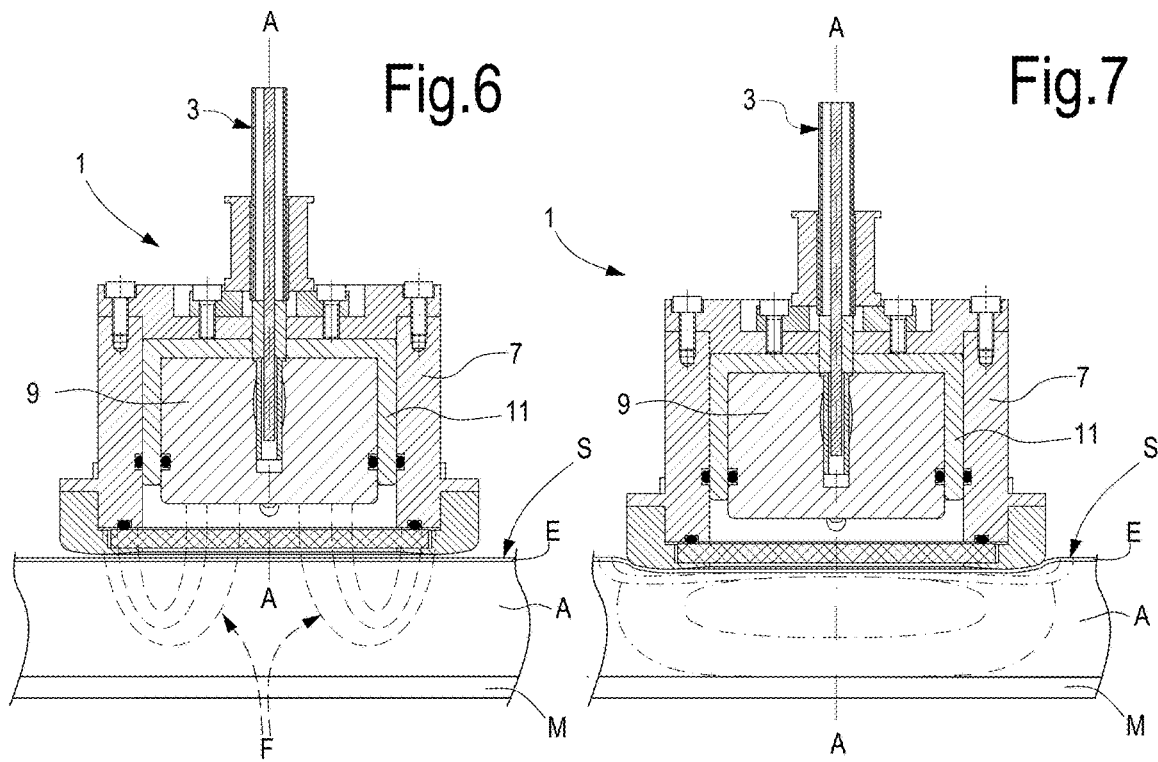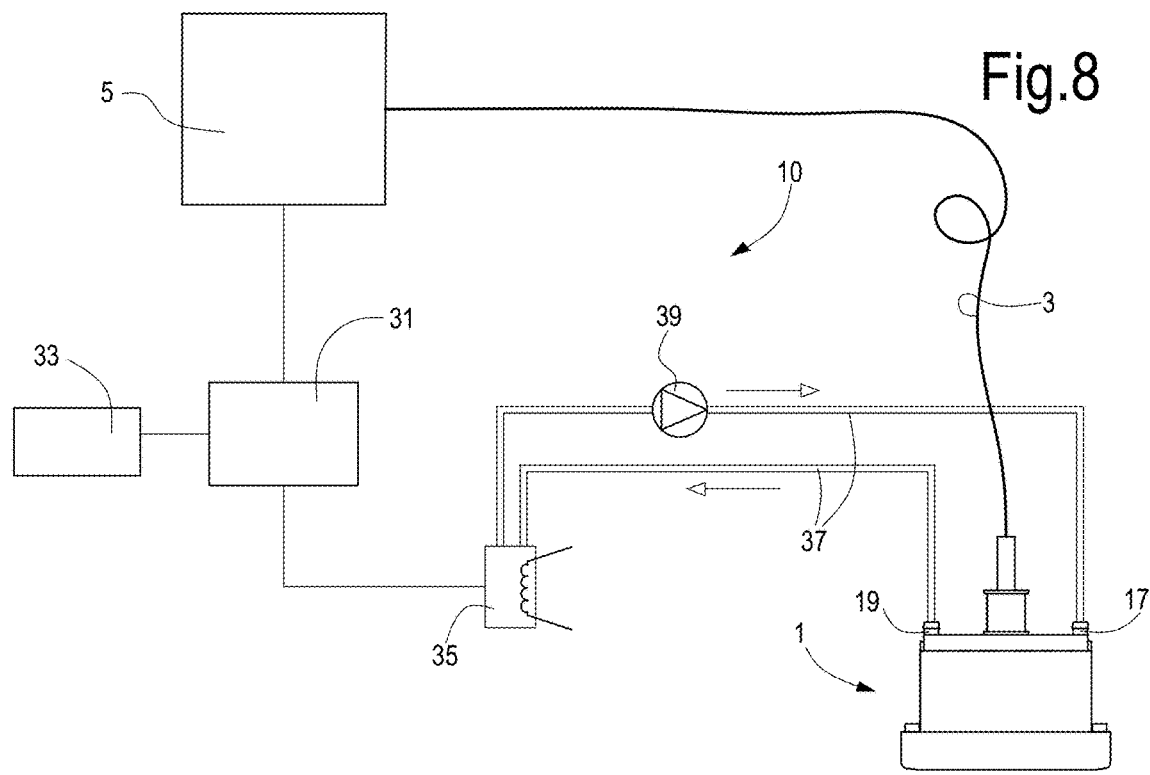

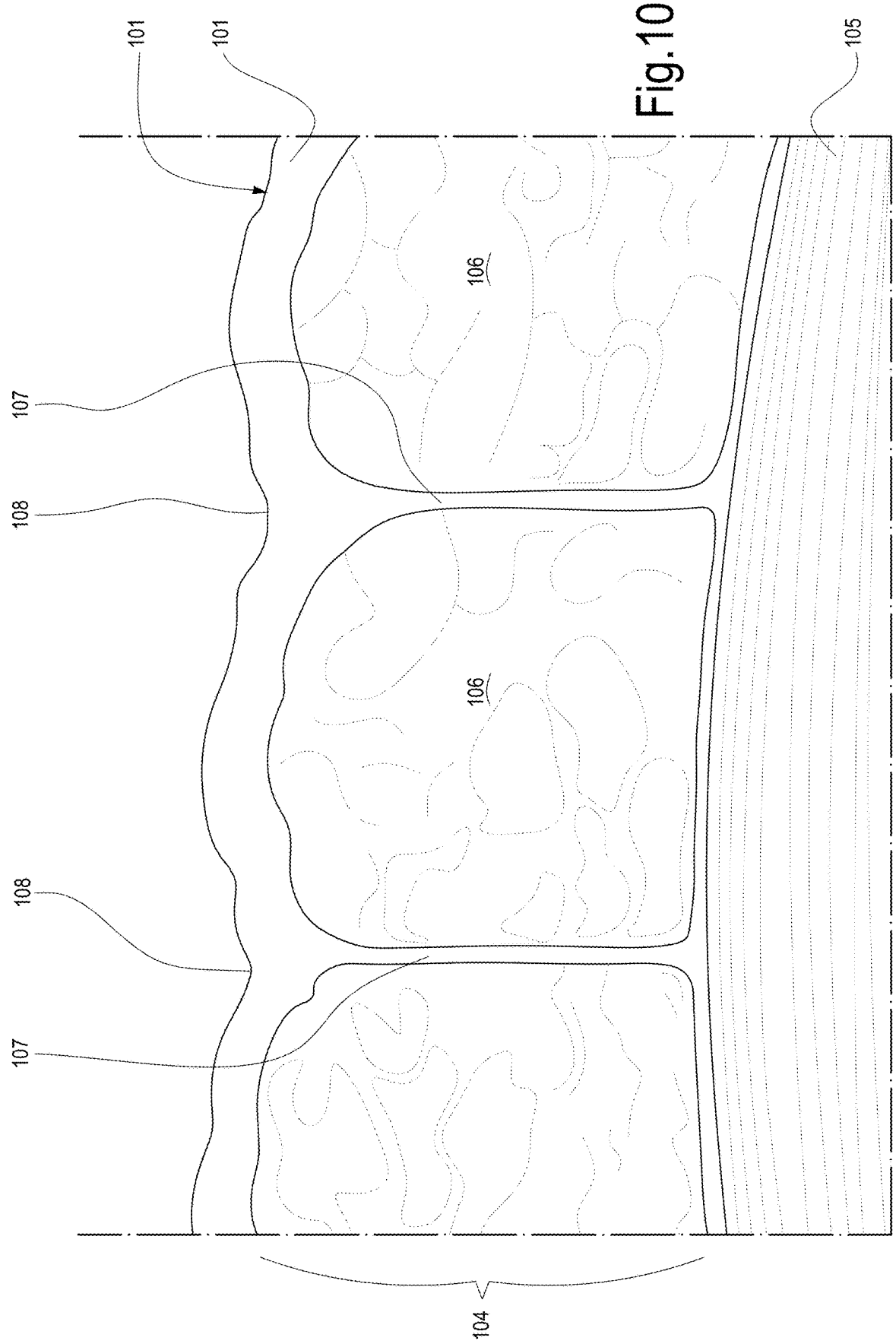

DELIVERY DEVICE WITH COAXIAL CABLE, APPARATUS COMPRISING SAID DEVICE AND METHOD

CROSS REFERENCE TO RELATED APPLICATIONS

This application is a continuation-in-part of U.S. patent application Ser. No. 16/081,631 filed Aug. 31, 2018, and claims the benefit (35 U.S.C. § 120 and 365(c)) of International Application PCT/IB2017/051215 filed Mar. 2, 2017, which designated inter alia the United States and claims the benefit of priority of Italian Patent Application UA2016A001370, filed Mar. 4, 2016, the entire contents of each application are incorporated herein by reference.

TECHNICAL FIELD

The present invention relates to medical devices and apparatuses. More in particular, the invention relates to improvements to devices and apparatuses for removing adipose layers.

BACKGROUND ART

Nowadays, in the aesthetical treatment field the techniques for selective removal of adipose tissue have great significance. To this end, various methods have been developed over the years, some of which are based on invasive surgery. In less recent times, a treatment called liposuction was widely used, allowing to eliminate fat portions through suction, wherein small cannulas are inserted through tiny cuts (some mm wide) in the skin achieving the adipose tissue to be removed or reduced and sucking fat. The suction may be performed manually by means of syringes, or using suitable sucking devices. In some cases, the suction may be combined with local application of ultrasounds, vibrations, or water jets in order better to liquefy fat.

As it is an invasive surgery, local or general anesthesia is used, based on the amount and distribution of the adipose tissue to be removed.

In some cases, in order to liquefy the adipose tissues a lipolysis treatment is performed, wherein liquids (for example soy lecithin) are injected into the adipose layers to be removed, the liquids being suitable to cause adipocytes lysis, i.e. the destruction of the cell membranes and therefore the liquefaction of adipocytes. The biological material resulting from lipolysis is then gradually absorbed by the organism.

More recently, laser-assisted liposuction techniques have been developed, wherein the adipocytes are sucked by means of a sucking cannula after having liquefied the fat by means of laser energy conveyed in the tissues by means of an optical fiber introduced through a cannula. In some cases, laser-assisted adipocytes lipolysis is performed and then the resulting biological material is metabolized by the organism instead of being removed by suction.

Methods and devices for laser-assisted lipolysis are disclosed in U.S. Pat. No. 6,206,873.

An alternative method uses cooling by means of plates surrounding folds of abdominal tissue constituted by derma and subcutaneous fat. The exposure to cooling for a certain time causes adipocytes damages and, thus, the cell death of subcutaneous fat tissue. The fat is then gradually eliminated by the organism.

Already in less recent times, methods have been proposed for adipocytes lipolysis by means of percutaneous energy delivery. U.S. Pat. No. 5,143,063 discloses, for example, an energy delivery device to be applied to the skin. The energy passes through the derma, achieves the underlying fat layers and causes adipocytes destruction. In this prior art document the use of different energy forms is disclosed, for example ultrasounds or microwave electromagnetic energy.

WO-A-96/40369 discloses an apparatus and a handpiece for fat removal through microwaves. The handpiece has a matrix of antennas generating converging microwave beams in order to achieve a desired temperature in the subcutaneous adipose layers.

EP-A-2767308 (corresponding to US-A) discloses devices and systems for microwave energy delivery in order to remove subcutaneous adipose layers. In an embodiment described in EP-A-2767308, a horn antenna is provided with an inner conductor of small diameter and a horn-shaped outer conductor of increasing diameter, ending with an edge whose diameter is more than tenfold greater than the diameter of the inner conductor. The horn-shaped outer conductor protrudes, with respect to the inner conductor, by a multiple of the inner conductor diameter.

These known devices for percutaneous delivery of radiant energy have the advantage of allowing substantially non-invasive treatments, but they are not particularly effective.

There is therefore the need for providing devices and apparatuses allowing lipolysis treatments that are non-invasive but effective.

Subcutaneous fat accumulations is also present in subjects affected by cellulite. Cellulite is a topographical alteration of the skin associated with depressions or introflexions, frequent in the pelvic and abdominal area, hips, buttocks and thighs. The typical unsightly appearance of cellulite is known as the "orange peel" effect, as the skin is covered in small indentations or dimples that resemble the skin of an orange. Orange peel skin consists of a series of fat accumulations (fat lobules) surrounded by bands of fibrous connective tissue (interlobular septa), present under the skin, which are also visible to the naked eye as they push up toward the outer skin layer causing a "bulging" effect.

SUMMARY OF THE INVENTION

According to a first aspect, a device for delivering radiofrequency energy is provided, comprising an outer conductor and an inner conductor arranged approximately coaxial with each other, wherein the outer conductor surrounds the inner conductor, so as to form an open-ended coaxial line. The open-ended coaxial line is connected, through a coaxial cable, for example, to a radiofrequency generator, typically a radiofrequency electromagnetic field generator. When connected to the radiofrequency generator, the outer conductor and the inner conductor, arranged and configured so as to form the open-ended coaxial line, generate an electromagnetic field with lines of force extending from a front surface of the inner conductor to a front surface of the outer conductor. When the open-ended coaxial line interfaces with the skin surface of a patient to be treated, the electromagnetic field spreads therefrom. By putting the delivery device into contact with the skin area where the underlying adipose layer shall be eliminated or removed (through a mechanism comprising adipocytes lysis and/or destruction by triggering of the apoptosis mechanism), an electric field propagates in the tissues below the area where the delivery device has been applied to the skin, according to lines of force extending approximately orthogonally with respect to the tissue layers, i.e. approximately orthogonally to the interface surfaces between epidermis and adipose layer, as well as between adipose layer and muscle tissue.

Consequently, the current crosses sequentially, i.e. serially, the various layers, causing greater heat dissipation and therefore greater heating in the tissues having more resistivity. These tissues are indeed the adipose layers, where, consequently, the transformation of electric energy into thermal energy is concentrated, with consequent localized temperature increase.

Practically, the delivery device may have an energy delivery window arranged in front of the outer conductor and the inner conductor. The delivery window may be embodied by a plate of a dielectric material which is transparent to the electromagnetic radiation frequency used for these applications. Advantageously, the used material is preferably also a good thermal conductor.

The window may be cooled, for instance by a coolant, which is dielectric in order to low electric losses and a good thermal conductor, and which flows along the inner surface of the closing plate, in order to avoid the risk of burns, as well as any feeling of localized overheating. In fact, the passage of radiofrequency energy through epidermis and derma causes therein heat production due to the transformation of electromagnetic energy into thermal energy and the consequent heating of the crossed tissues. The cooled window into contact with the epidermis removes heat and keeps the tissue temperature within acceptable values.

According to a further aspect, the invention also relates to a radiofrequency energy delivering apparatus, comprising a radiofrequency generator, a connector and a delivery device as described above.

According to a further aspect, a method is described for removing adipose layers, comprising the following steps:

applying a delivery device of the type described above to an epidermis portion, below which the adipose layers to be eliminated or reduced are located;

by means of the delivery device generating a radiofrequency electromagnetic field in a tissue volume below the epidermis portion, which has lines of force that extend approximately orthogonally with respect to the epidermis and that sequentially cross the epidermis, the derma and the adipose tissue below the derma.

In this way, a current flow is generated by the electromagnetic field, causing localized heating of the adipose tissue up to a temperature sufficient to cause the immediate lysis of some adipocytes and/or the subsequent destruction, through the apoptosis mechanism, of at least part of the adipocytes forming the adipose tissue.

Further advantageous features and embodiments of the delivery device, of the apparatus using it, and of the method according to the invention are described hereafter with reference to the attached drawing, which shows a non-limiting practical embodiment of the invention, and in the attached claims, forming an integral part of the present description.

BRIEF DESCRIPTION OF THE DRAWING

The invention will be better understood by following the description and the accompanying drawing, which shows non-limiting practical embodiments of the invention. More particularly, in the drawing:

FIG. 3 shows a plan view of the device of FIGS. 1 and 2;

FIGS. 4 and 5 are cross-sections according to IV-IV and V-V of FIG. 3;

FIG. 6 schematically shows the pattern of the lines of the electric field generated by the delivery device of FIG. 1;

FIG. 7 shows a simulation of the temperature distribution inside tissues during the treatment;

FIG. 8 shows a block diagram of an apparatus using the delivery device of FIG. 1;

FIG. 10 shows a schematic cross-sectional view of a portion of epidermis and underlying fat lobules, surrounded by bands of fibrous connective tissue, forming interlobular septa.

DETAILED DESCRIPTION OF EMBODIMENTS

The following detailed description of the exemplary embodiments refers to the accompanying drawings. The same reference numbers in different drawings identify the same or similar elements. Additionally, the drawings are not necessarily drawn to scale. Also, the following detailed description does not limit the invention. Instead, the scope of the invention is defined by the appended claims.

Reference throughout the specification to "one embodiment" or "an embodiment" or "some embodiments" means that the particular feature, structure or characteristic described in connection with an embodiment is included in at least one embodiment of the subject matter disclosed. Thus, the appearance of the phrase "in one embodiment" or "in an embodiment" or "in some embodiments" in various places throughout the specification is not necessarily referring to the same embodiment(s). Further, the particular features, structures or characteristics may be combined in any suitable manner in one or more embodiments.

Figure 1:
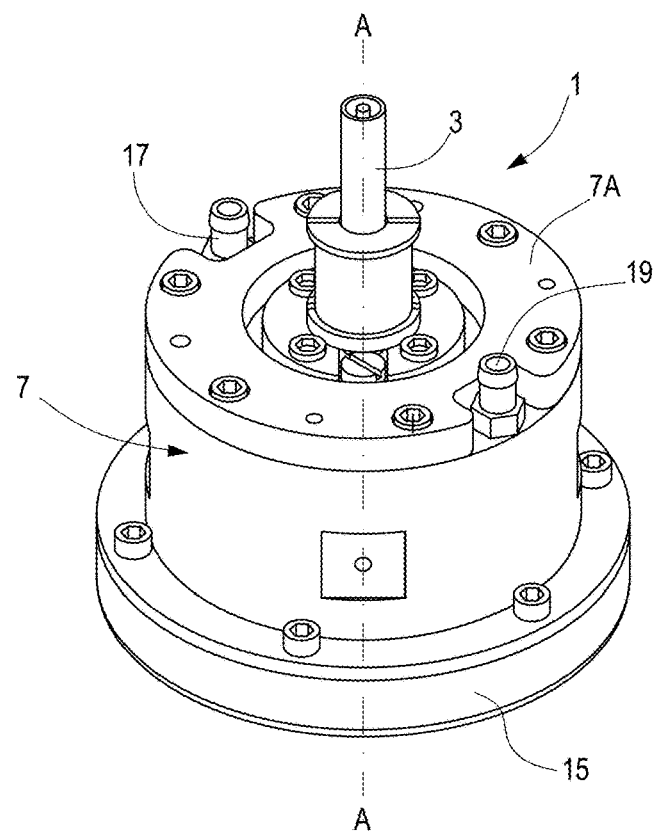
FIG. 1 shows an axonometric view from the top of an embodiment of a delivery device according to the invention.
Figure 2:
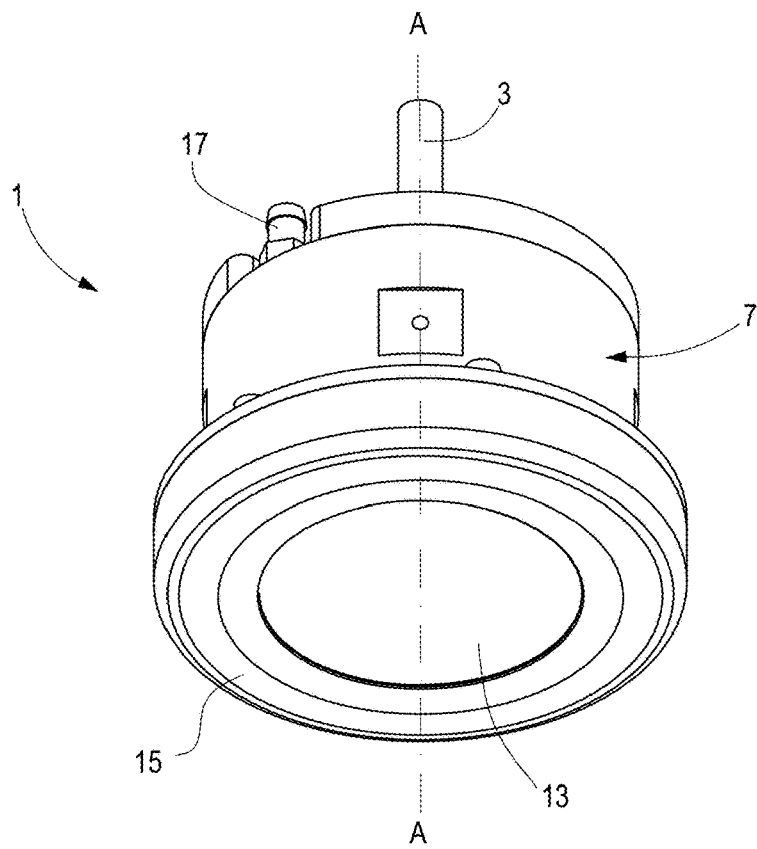
FIG. 2 shows an axonometric view from the bottom of the device of FIG. 1.

With initial reference to FIG. 1, in some embodiments a delivery device is provided, also called handpiece and indicated as a whole with number 1. The delivery device 1 is connected to a radiofrequency generator, schematically indicated with number 5 in FIG. 8, by means of a cable, for example a coaxial cable 3.

In the embodiment of FIG. 1, the delivery device 1 comprises an outer conductor 7 and an inner conductor 9, substantially coaxial with each other, the outer conductor 7 defining a seat or cavity, inside which the inner conductor 9 is housed. Preferably, the conductor 7 is coupled to an outer conductor, usually called "shield" of the coaxial cable 3, and the inner conductor 9 is coupled to the inner conductor of the coaxial cable 3. In this way, the outer conductor 7 of the delivery device 1 is grounded and may be held by an operator without electrocution risk.

The inner conductor 9 has a front surface 9A facing towards the outside.

The conductors 7 and 9 form a coaxial line with an open end and a closed end at the exit of the coaxial cable 3 for the connection to the radiofrequency generator.

The outer conductor 7 may be cup-shaped and may have a first end 7A formed by a cover and substantially closed, except for the presence of a central hole allowing the passage of the center conductor 3C of the coaxial cable 3, and particularly the dielectric interposed between shield and center conductor and the same center conductor. The end 7A forms the bottom of the cup. The reference number 7B indicates an opposite open end having a substantially annular front surface 7C. The outer conductor 7 defines an inner space 8 where the inner conductor 9 is housed and contained. The inner conductor 9 can be held in a position approximately coaxial with the outer conductor 7. For example, an insert may be provided, made of low-loss dielectric material 11, interposed between the outer conductor 7 and the inner conductor 9.

The inner conductor 9 may be constituted by a solid cylindrical element.

The open end 7B of the outer conductor 7 defines a window delimited by the front surface 7C.

The front surface 7C of the outer conductor 7 and the front surface 9A of the inner conductor 9 have a reciprocal distance in axial direction indicated with "d". In other words, the front surface 7C of the outer conductor 7 protrudes in axial direction by a distance "d" with respect to the front surface 9A of the inner conductor 9. This distance is practically the distance between two parallel planes containing the front surface 9A and the front surface 7C respectively.

The front surfaces 9A and 7C are preferably flat, except for the presence of grooves suitable to receive sealing rings, as shown in the drawing. In order to have a better distribution of the electric field lines, the surfaces 9A and 7C have preferably low roughness. They can be, for example, lapped or polished surfaces.

Preferably, in order to have a better coupling between the electric field, generated by the delivery device, and the patient's body subjected to lipolysis, the distance "d" is advantageously lower than the outer diameter D9 (see FIGS. 4 and 5) of the inner conductor 9, preferably equal to or lower than approximately the half of the diameter D9. Preferably, the distance "d" is equal to or lower than ¼ of the outer diameter D9 of the inner conductor 9. More preferably, the distance "d" is lower than approximately ⅕ of the diameter D9. For instance, the distance "d" is equal to or lower than approximately ⅛ of the diameter D9. Even if in the embodiment of FIGS. 1-7 the distance "d" is different than zero, however it may also be equal to zero, i.e. the surfaces 9A and 7C may be substantially coplanar. It is therefore possible to provide a delivery device 1 wherein the distance "d" is comprised between zero and a maximum value as indicated above.

In some embodiments, the outer conductor 7 may have a front surface 7C that is arranged backwards with respect to the front surface 9A of the inner conductor 9.

The distance "d" in axial direction between the surfaces 7C and 9A is kept small in order to achieve an effective operation of the device. In fact, in this way the electric field lines extending between the front surface 9A of the inner conductor 9 and the front surface 7C of the outer conductor 7 mostly propagate outside the volume defined by the outer conductor 7 and arrange themselves orthogonally to the above-mentioned front surfaces. This is an advantage because, as will be better detailed below, in this way an optimal current flow is generated in the treated tissues, which achieves the adipose layers where the thermal increase is required in order to liquefy the adipose cells.

In FIGS. 4 and 5, D7 indicates the inner diameter of the outer conductor 7, i.e. the diameter of the inner space 8, where the conductor 9 is housed. In advantageous embodiments, in order to optimize the shape of the electric field lines extending from the delivery device towards the tissues to be treated, and in order to have an effective coupling with the tissues, the ratio between D7 and D9 should be not too high, i.e. the surfaces 9A and 7C should be not too much distant from each other in radial direction, i.e. in a direction orthogonal to the axis A-A of the delivery device 1. In advantageous embodiments, the ratio R defined as R=D7/D9, i.e. the ratio between the inner diameter D7 of the outer conductor 7 and the outer diameter D9 of the inner conductor 9, is comprised between approximately 1 and approximately 2, preferably between approximately 1.1 and approximately 1.7, and more preferably between approximately 1.2 and approximately 1.5.

The inner space 8 may be closed at the front by means of a wall transparent to the electromagnetic radiation used, so as to allow the propagation of an electromagnetic field through the transparent wall. For example, the transparent wall may comprise a plate 13 made of sapphire (alumina $Al_2O_3$ and other atoms in low percentage) or other suitable dielectric material with good heat conductivity. The plate 13 may be fastened to the outer conductor 7 by means of a flange 15. The plate 13 is advantageously configured so as to be in contact with the epidermis of a patient, to whom the radiofrequency energy shall be delivered for lipolysis treatment.

In some embodiments, the delivery device 1 comprises a cooling system, so configured as to remove heat from the plate 13, during the use of the delivery device 1, thus limiting the temperature of the epidermis and the derma that are heated due to the dissipation of the electromagnetic energy flowing therethrough, and thus avoiding burns or troubles for the patient.

In the illustrated embodiment, the cooling system comprises a coolant inlet duct (17) and a coolant outlet duct (19). The coolant flowing ducts 17, 19 may extend parallel to the axis A-A of the delivery device 1. In advantageous embodiments, the coolant flowing ducts 17, 19 are provided in the outer conductor 7 or they are housed in seats provided in the thickness of the outer conductor 7, as shown in FIG. 5.

The number of coolant flowing ducts may be different than that represented, for example in order to have a more efficient coolant circulation. The coolant may be gaseous or, preferably, liquid.

In the illustrated embodiment, the two coolant flowing ducts 17, 19 are fluidly coupled through a gap 21 provided between the plate 13 and the front surface 9A of the inner conductor 9 facing towards the plate 13.

With this arrangement, the coolant can circulate in the gap 21 so as to remove heat from the plate 13 through forced convection, and to keep the outer surface of the plate at a sufficiently low temperature to avoid burns or just an overheating feeling for the patients.

FIG. 6 schematically shows the operation of the delivery device 1 applied to the patient's epidermis surface. The letter S indicates the outer surface, the letter E indicates the epidermis layer, the letter A indicates the adipose tissue layer formed by the adipocytes that shall be at least partially removed, and the letter M indicates the muscle layer below. The figure is schematic and not necessary scaled. The interface surfaces between the various layers are indicated as flat surfaces for the sake of simplicity of drawing, even if in the reality they can be different, for example the derma and the adipose layer may have a variable thickness.

The lines of force, or field lines, of the electric field generated by the radiofrequency current supplied through the coaxial cable 3 are indicated with the letter F. They extend from one to the other of the inner conductor 9 and the outer conductor 7. More in particular, the lines of force F extend from the front surface 9A of the inner conductor 9 and close on the front surface 7C of the outer conductor 7. As it is well known, the electric field lines arrange themselves orthogonally to the surface of the conductor by which they have been generated. Therefore, the electric field lines F are orthogonal to the front surface 9A of the inner conductor 9 and to the front surface 7C of the outer conductor 7. This orthogonality of the field lines is optimized by making these surfaces with low roughness, for example by lapping or polishing them. In this way, the field lines are not deformed in correspondence of any roughness.

As it is easily understood from the schematic view of FIG. 6, when the delivery device rests on the epidermis E, the lines of force F are approximately orthogonal to the epidermis surface S, and therefore they sequentially cross the layers E, A, and M. The current induced by the electromagnetic field circulates in the same direction.

From an electric point of view, the layers E, A and M may be considered as electric impedances arranged in series, thus crossed by the same current (induction and displacement current) induced by the electromagnetic field generated by the open-ended coaxial cable.

The resistive part of the impedance of the adipose tissue A is greater than the resistive part of the impedance of the epidermis and the derma E, as well as of the muscle layers M, so that the energy conveyed by the electric field exiting from the two coaxial conductors 7, 9 is dissipated to a greater extent in the adipose tissue and to a lesser extent in the adjacent layers. Therefore, in the adipose tissues a greater energy amount is deposited, causing a localized heating of the adipose tissue up to a temperature greater than the temperature achieved by the adjacent tissues (epidermis, derma and muscles). In this way, a greater efficiency of the delivery device 1 is provided with respect to other devices (for example of the radiative type) where the electromagnetic field is polarized parallel to the tissue stratification. In these delivery devices, the tissue stratification behaves like an arrangement of resistances in parallel. In this way, the current preferably flows in the tissue with lower resistance (skin and muscle), with consequently greater heating of these layers, and lower efficiency of the delivery device, as well as with more troubles for the patient.

FIG. 7 schematically shows a temperature distribution obtained by means of thermal simulation. The isotherms show the temperature field in the tissue layers below the delivery device. The lowest temperature is that of the skin, partially because of the reduced energy dissipation due to the low resistivity of the epidermis, and mainly because of the effect of cooling achieved through the cooling system incorporated in the delivery device. The highest temperature is achieved in the adipose layer, because of the high resistive part of the electric impedance of this tissue, and therefore of the high amount of electric power converted into heat.

The dimension of the components of the delivery device 1 may be selected suitably, for example based on the body part to be treated. Smaller delivery devices may be provided for treating small body areas and/or body areas that are more difficult to be achieved, for example the inner thigh. Larger delivery devices may be used for treating larger areas and/or more accessible areas, such as abdomen, back and buttocks.

The open-ended coaxial line conformation of the conductors 7 and 9 is such that, when the delivery device is moved away from the body surface, the power supply stops, as the coaxial cable is designed so as to have a characteristic impedance suitable for biological tissues, and therefore the electromagnetic field cannot propagate in the air constituting an unmatched load. This makes the device 1 intrinsically safe.

FIG. 8 shows a general scheme of an apparatus 10, with which the delivery device 1 described above can be used. The apparatus 10 comprises, in addition to the radiofrequency generator 5, a central control unit 31 connected to the generator 5 and to one or more user interfaces, schematically represented by the block 33. Moreover, the central control unit 31 may be connected to a cooling unit 35 for the coolant flowing in the gap 21 of the delivery device 1. Number 37 indicates the inlet and outlet pipes connecting the delivery device 1 to the cooling unit 35. The coolant circulates by means of a pump 39. In the cooling unit 35 a cooling system with an air exchanger may be provided, or a Peltier cooler, or any other cooling system with sufficient capacity to dissipate the heat extracted by the coolant from the delivery device 1.

The radiofrequency generator may be configured so as to generate current at a frequency comprised between approximately 2 GHz and approximately 6 GHz, preferably between approximately 2.3 GHz and approximately 5.2 GHz, more preferably between approximately 2.3 GHz and approximately 3 GHz, even more preferably about 2.4-2.5 GHz.

The apparatus 10 with the delivery device 1 may be used to implement a method for reducing the mass of fat tissues as follows. The radiofrequency generator 5 is actuated and the delivery device 1 is put onto the epidermis portion, below which the adipose tissue to be eliminated or reduced is located. As mentioned above, the radiofrequency generator 5 may be actuated even before putting the delivery device 1 onto the skin, as substantially no radiations are emitted from the open-ended coaxial line formed by the conductors 7 and 9 until it is coupled to the epidermis.

Once the delivery device 1 has been put into contact with the epidermis, with the use, if necessary, of a thin layer of gel or biocompatible oils facilitating the coupling, the delivery device 1 may be kept still for a certain time. Alternatively, the delivery device 1 may be moved at a suitable speed, manually or through a scanning system, not shown, so as to treat a portion of surface S of epidermis E larger than the contact area of the delivery device 1, substantially defined by the window formed by the plate 13.

If the delivery device 1 is kept fixed in a given position, the power delivered to the epidermis and the time the delivery device remains in position are such as to achieve a temperature in the adipose tissue that is suitable to trigger apoptosis and/or other adipose cell destruction mechanisms. Preferably, the temperature is sufficiently low to avoid significant tissue denaturation effects. In some embodiments, the temperature achieved in the adipose tissue to be treated may be comprised between approximately 40° C. and approximately 50° C., preferably between approximately 42° C. and approximately 47° C. The power delivered by the electromagnetic field may be comprised between approximately 10 W and approximately 150 W, preferably between approximately 20 W and approximately 130 W, more preferably between approximately 30 W and approximately 110 W. In other embodiments, the delivered power may be comprised between approximately 70 W and approximately 150 W, preferably between approximately 90 W and approximately 130 W, more preferably between approximately 95 W and approximately 110 W.

With this order of magnitude, and taking into account the heat dissipation from the tissues due to thermal diffusion and thermoregulation of the blood system, the time the delivery device 1 can remain on a given treatment area may be comprised between approximately 5 and approximately 20 minutes, preferably between approximately 7 and approximately 15 minutes, more preferably between approximately 8 and approximately 12 minutes.

During the treatment it is possible to detect the epidermis surface temperature through a temperature sensor, not shown, that may be integrated in the delivery device and interfaced with the central control unit 31. The control unit may also modulate the delivered power and/or it may act on the parameters of the cooling system, so as to keep the epidermis surface temperature at a suitable preset value. This value may be lower than the body temperature, in order to protect the whole derma against over-temperatures. The central control unit may be programmed, for example, so as to decrease or increase the temperature of the coolant supplied to the inlet duct 17, based on the detected temperature and on an error signal caused by a difference between the preset temperature and the temperature detected on the epidermis.

Moreover, the central control unit 31 may be programmed so as to interrupt the delivered power if, for example because of a fault, the cooling system stops working or is not sufficient to keep the epidermis temperature at the preset value. If the epidermis temperature is higher than that required, in spite of an increase in the coolant flow rate and/or a decrease in the coolant temperature, the central control unit 31 may be programmed so as to be actuated secondarily, reducing the delivered radiofrequency power also if it has exceeded the preset limits because of a fault or an error by the operator. These last two cases (faults of the cooling system or of the radiofrequency energy delivery system) may act simultaneously also actuating the alarm for the operator.

The operator may be also alerted if, due to a fault or an error, the correct trend of the temperatures is not measured as it should occur if the treatment would be performed according to the temperature range and the corresponding dynamics are not respected.

The detected parameters, the treatment duration, the estimated temperature in the adipose tissues, the overall delivered energy, the instant power, and other parameters may be displayed on the user interface 33 that, to this end, may comprise a monitor, a display or other displaying devices. The central control unit 31 may be also programmed so as to interrupt the delivery when a given preset delivery time has been achieved, or when a given threshold of total delivered energy has been achieved.

As mentioned with reference to FIG. 7 and to the shape of the electric field lines F, during the treatment the displacement and conduction current inside the tissues is such that the the same amount of current flows in series through each single layer E, A, M. Consequently, the adipose layer A, having the higher losses, is the layer where the greater amount of energy will be dissipated in the form of heat. The radiofrequency energy delivery is stopped by interrupting the power supply to the generator 5, or simply by decoupling the delivery device 1 from the epidermis, when it has been evaluated that in the adipose tissues a sufficient temperature has been achieved, and has been kept for a suitable time, to cause the effects required for removing at least part of the adipocytes.

The power is distributed by the coaxial line 7, 9 according to an approximately cylindrical volume under the epidermis in the area directly adjacent to the delivery device 1, with a heat distribution having a maximum at a depth that may be preset when the delivery device is dimensioned. This is an intrinsic feature of the morphology of the delivery device with open-ended coaxial cable. In this way, if the area of the window 13 of the delivery device 1 is lower than what is necessary for treating the whole volume where the temperature increase is required for reducing the number of adipocytes, the process may be repeated for subsequent areas, if necessary also marking on the epidermis the already treated areas, in order to avoid a repeated exposure of the same volumes to radiofrequency.

The adipocyte damage caused by the localized temperature increase in the adipose tissues practically causes the adipocytes to be transformed into compounds that are subsequently absorbed and metabolized by the organism.

However, it is also possible to intervene later with a step of sucking the liquid resulting from lipolysis by means of suction cannulas according to some currently used methods.

In the embodiment of the delivery device 1 illustrated in detail in FIGS. 4-7, a gap 21 is provided between the front surface 9A of the inner conductor 9 and the inner surface of the plate 13. This gap allows an efficient circulation of a coolant in order to avoid overheating the patient's epidermis during treatment. However, the presence of the gap 21 requires a distance "d" (FIGS. 4 and 5) between the front surfaces 9A and 7C, which can affect the electric efficiency of the delivery device 1.

In some embodiments, it is preferable to decrease this distance as most as possible, even to reduce it to zero. For example, in some embodiments, the cooling circuit may be configured so as to avoid the presence of the cooling gap 21.

Figure 9:
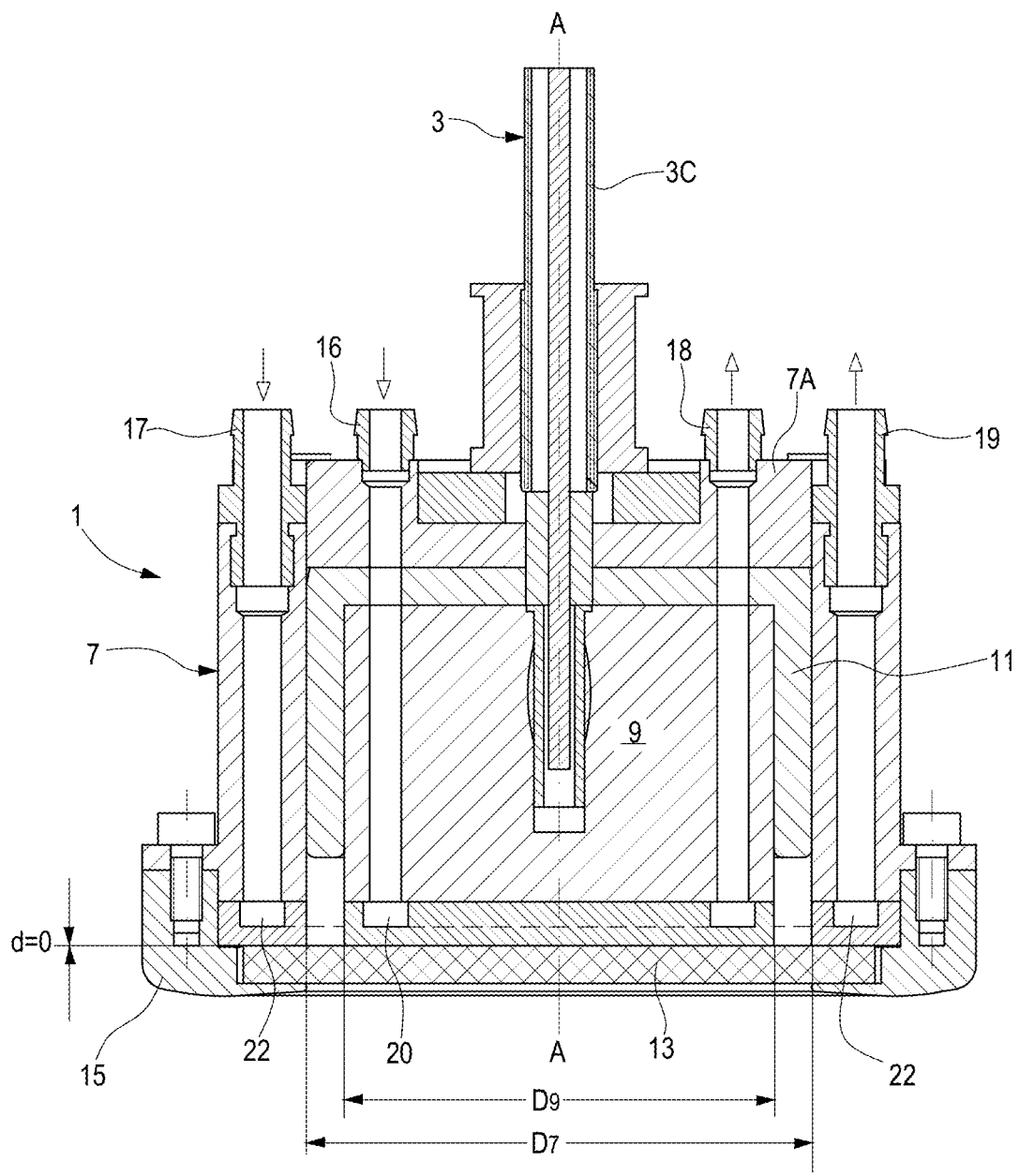
FIG. 9 shows a longitudinal cross-section of a further embodiment of the delivery device.

FIG. 9 shows a cross-section according to a plane containing the axis A-A of an embodiment of the delivery device 1, wherein the gap 21 has been eliminated or substantially eliminated. In this embodiment, the distance "d" in axial direction between the planes where the surfaces 9A and 7C lie may be therefore substantially smaller than in the embodiment of FIGS. 4 and 5. In some cases, the distance "d" may be approximately equal to zero.

In some embodiments, the delivery device 1 may be not cooled, or the cooling may be performed by means of a cooling system (not shown) arranged outside the outer conductor 7. In further embodiments, as schematically shown in FIG. 9, the cooling may be performed by means of coolant flowing ducts formed inside the outer conductor 7 and the inner conductor 9. For example, the inlet and outlet ducts 17 and 19, already described with reference to FIGS. 4 and 5, may be fluidly coupled to an annular front duct 22, confined inside the outer conductor 7 adjacent to the front surface 7C. Two or more inlet and outlet ducts 16 and 18 may be provided in the inner conductor 9 for flowing the coolant in an annular duct 20, or in a gap, or in a network of cooling ducts, formed inside the inner conductor 9 near the front surface 9A thereof.

In order to facilitate manufacturing of the cooling ducts adjacent to the front surfaces 7C and 9A, the front portions of the conductors 7 and 9 may be formed by mechanical components separate with respect to a cylindrical body forming the main portion of the respective conductor.

In case there is no gap 21 where a fluid (which can be pressurized) flows, the plate 13, which closes the inner space 8 where the inner conductor 9 is housed, may be thinner. In some cases, the plate 13 may be omitted. In some embodiments, instead of the plate 13 a thin laminar interchangeable element may be provided, applied frontally in order to protect the delivery device 1 and to avoid, for example, the penetration in the delivery device 1 of dirt or of any gel applied on the delivery device 1 to improve the coupling thereof with the patient's body. By reducing the thickness of the plate 13, or by eliminating the plate, it is possible to have a better coupling between the electric field and the tissues to be treated.

The lack of fluid circulation between the outer conductor 7 and the inner conductor 9 allows to eliminate the seal formed on the front surface 7C of the outer conductor 7 and therefore also to eliminate the annular groove provided for housing it. This allows to have a completely flat front surface 7C, which optimizes the pattern of the electric field lines.

It has now been discovered that treatment of subcutaneous fat by irradiation of the subcutaneous tissue layers with microwaves generated by the coaxial cable, as described above, has a surprising and unexpected effect on the orange peel skin in a patient affected by cellulite.

Cellulite is a change in skin structure and appearance, presenting a dimpled or "orange peel" surface. The outermost layer of skin is referred to as the epidermis. Immediately under this epithelial tissue, there is the dermis, a connective tissue richly filled with hair follicles, sweat glands, blood vessels and nerve receptors. The next, deeper one is the subcutaneous layer mainly constituted by fat. Clusters of fat cells are constituting lobules, surrounded by interlobular collagen septa. The prevailing evidence-based understanding is that cellulite originates in the most superficial part of subcutaneous fat, where fat cell chambers [lobules] are arranged vertically in females, separated by fibrous cords of connective tissue particularly rich in compacted collagen fibers. From the most superficial and bigger fat lobules in the subcutaneous tissue, clusters of fat cells protrude into the dermis pushing it up against the epidermis raising the corresponding skin areas. This mechanism is closely associated to the pulling down of the long interlobular septa formed by highly compacted collagen. All this creates an uneven and dimpling surface of the skin, often referred to as cellulite.

FIG. 10 shows a schematic cross-sectional view of a portion of epidermis and underlying tissue structures thereof. More specifically, reference number 100 designates the epidermis and reference number 101 designates the underlying derma. The subcutaneous fat layer is shown at 104. The muscles are shown at 105. The clusters of fat cells constituting the lobules are shown at 106, while reference number 107 designate the interlobular collagen septa. The dimpling surface of the skin is shown at 108.

At the same time with the expression of molecular mechanisms involving adipocytes and responsible of adipolysis, following treatment with microwave radiation generated by the above described co-axial cable emitter, an involvement of the connective tissue constituting the interlobular septa has been observed, particularly apparent on the thicker and fibrotic bundles of collagen fibers forming the interlobular septa 107 between bigger adipose lobules 106.

FIGS. 11(A), 11(B), 11(C) and 11(D) show histological images of skin samples (epidermis and dermis), including subcutaneous tissue (extremely rich of adipose cells), stained with hematoxylin and Picrosirius Red (PR), which is a specific stain for collagen fibers in the connective tissue. In FIGS. 11(A)-(D) the stained collagen fibers are visible as dark-gray areas.

Figure 11A:
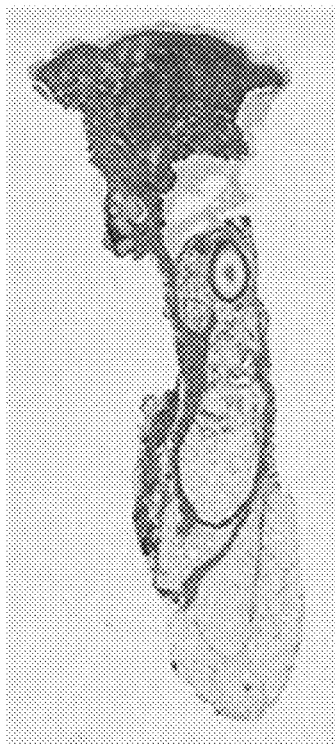
FIGS. 11A, 11B, 11C, 11D show histological images illustrating the effect of microwave electromagnetic irradiation on the interlobular septa.

More specifically:

FIG. 11(A) illustrates the Baseline (control): no microwave application has been performed. In the subcutaneous tissue adipose tissue cells (adipocytes) appear white (not stained), while interlobular connective tissue septa appear as thick cords intensely stained (dark gray).

Figure 11B:
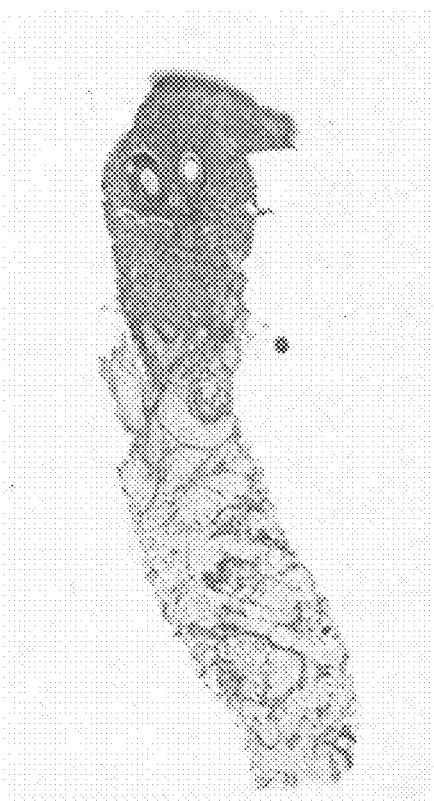

FIG. 11(B) illustrates a tissue sample immediately after microwave treatment. In the subcutaneous adipose tissue, interlobular septa appear thinner and fragmented compared to FIG. 11(A) (baseline/control).

Figure 11C:
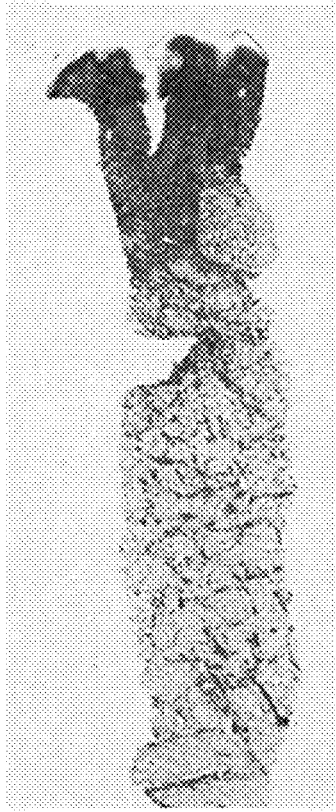

FIG. 11(C) illustrates an image of a treated tissue sample taken one hour after microwave treatment. In the subcutaneous adipose tissue, interlobular septa appear less and less thick and highly fragmented.

Figure 11D:

FIG. 11(D) illustrates an image of a treated tissue sample taken six hours after microwave treatment. In the subcutaneous adipose tissue, interlobular septa are extremely thin and fragmented. Collagen fibers appear extremely thin and they never form thick bundles, differently from FIG. 11(A) (base/control), where bundles in form of fibrous cords are clearly visible. The structural bases responsible for the orange/peel skin surface, namely the collagen interlobular septa, are dissolved or destroyed.

The destruction of interlobular connective tissue septa 107 (FIG. 10), possibly accompanied by lysis of the adipose cells results in an immediate amelioration of the aesthetic appearance of skin, with an immediate reduction of the orange peel effect.

What is claimed is:

1. A method for reducing orange peel skin effect in a subject affected by cellulite, the method comprising the following steps:
    applying a delivery device to an epidermis portion, the delivery device comprising:
        an outer conductor and an inner conductor arranged approximately coaxial with each other, the outer conductor surrounding the inner conductor, wherein the outer conductor and the inner conductor form an open-ended coaxial line, the inner conductor having a front surface and the outer conductor having an annular front surface, wherein the front surface of the inner conductor and the annular front surface of the outer conductor are arranged at a distance from one another in an axial direction not greater than a diameter of the inner conductor;
        an energy delivery window, arranged in front of the outer conductor and the inner conductor, wherein the outer conductor and the inner conductor are configured to generate an electric field with lines of force extending from the front surface of the inner conductor to the annular front surface of the outer conductor when the energy delivery window is applied to the epidermis portion;
    generating, by the delivery device, the electric field in a tissue volume below the epidermis portion, across derma and adipose tissue under the derma, said adipose tissue including fat lobules and interlobular septa formed by fibrous connective tissue, wherein lines of force of the electric field extend approximately orthogonally to interface surfaces between epidermis and adipose layer, as well as between adipose layer and muscle tissue;
    at least partly dissolving said interlobular septa by action of heat generated by the electric field.

2. The method of claim 1, further comprising the step of causing a localized heating of the adipose tissue up to a temperature sufficient to cause destruction of at least part of the adipocytes forming said adipose tissue.

3. The method of claim 1, wherein the electric field is generated only when the energy delivery window is applied to the epidermis portion.

4. A method for reducing orange peel skin effect in a subject affected by cellulite, the method comprising the following steps:
    applying a delivery device to an epidermis portion, the delivery device comprising:
        an outer conductor and an inner conductor arranged approximately coaxial with each other, the outer conductor surrounding the inner conductor, wherein the outer conductor and the inner conductor form an open-ended coaxial line, the inner conductor having a front surface and the outer conductor having an annular front surface, wherein the front surface of the inner conductor and the annular front surface of the outer conductor are arranged at a distance from one another in an axial direction not greater than a diameter of the inner conductor;

an energy delivery window, arranged in front of the outer conductor and the inner conductor, wherein the outer conductor and the inner conductor are configured to generate an electrical flow path extending from the outer conductor to the inner conductor when the energy delivery window is applied to the epidermis portion;

generating, by the delivery device, the electrical flow path such that the electrical flow path includes a tissue electrical flow path portion extending in a tissue volume below the epidermis portion, across derma and adipose tissue under the derma, said adipose tissue including fat lobules and interlobular septa formed by fibrous connective tissue, wherein at least a portion of the tissue electrical flow path portion extends approximately orthogonally to interface surfaces between epidermis and adipose layer, as well as between adipose layer and muscle tissue;

at least partly dissolving said interlobular septa by action of heat generated by the electrical flow path.

5. The method of claim 4, further comprising the step of causing a localized heating of the adipose tissue up to a temperature sufficient to cause destruction of at least part of the adipocytes forming said adipose tissue.

6. The method of claim 4, wherein the electrical flow path is generated only when the energy delivery window is applied to the epidermis portion.

7. A method for reducing orange peel skin effect in a subject affected by cellulite, the method comprising the following steps:

applying a delivery device to an epidermis portion, the delivery device comprising:

an outer conductor and an inner conductor arranged approximately coaxial with each other, the outer conductor surrounding the inner conductor, wherein the outer conductor and the inner conductor form an open-ended coaxial line, the inner conductor having a front inner conductor surface, the outer conductor having a front outer conductor surface, the front inner conductor surface and the front outer conductor surface being arranged at a distance from one another in an axial direction not greater than a diameter of the inner conductor;

an energy delivery window, arranged in front of the outer conductor and the inner conductor, wherein the outer conductor and the inner conductor are configured to generate an electric field extending from the front inner conductor surface to the front outer conductor surface when the energy delivery window is applied to the epidermis portion;

generating, by the delivery device, the electric field such that a portion of the electric field is in a tissue volume below the epidermis portion, across derma and adipose tissue under the derma, said adipose tissue including fat lobules and interlobular septa formed by fibrous connective tissue, wherein the portion of the electric field in the tissue comprises lines of force, the lines of force being approximately orthogonally to interface surfaces between epidermis and adipose layer, as well as between adipose layer and muscle tissue;

at least partly dissolving said interlobular septa by action of heat generated by the electric field.

8. The method of claim 7, further comprising the step of causing a localized heating of the adipose tissue up to a temperature sufficient to cause destruction of at least part of the adipocytes forming said adipose tissue.

9. The method of claim 7, wherein the electric field is generated only when the energy delivery window is applied to the epidermis portion.

10. The method of claim 7, wherein the front outer conductor surface is annular.

\* \* \* \* \*